US012758453B2

(12) United States Patent
Coppens et al.

(10) Patent No.: US 12,758,453 B2
(45) **Date of Patent: *Oct. 13, 2026**

(54) MRI COMPATIBLE AIR MANAGEMENT SYSTEM

(71) Applicant: Qfix Systems, LLC, Avondale, PA (US)

(72) Inventors: Daniel Coppens, Avondale, PA (US); James Manning, Newark, DE (US); Franklin Ports, Jr., Conowingo, MD (US)

(73) Assignee: Qfix Systems, LLC, Avondale, PA (US)

(*) Notice: Subject to any disclaimer, the term of this patent is extended or adjusted under 35 U.S.C. 154(b) by 41 days.

This patent is subject to a terminal disclaimer.

(21) Appl. No.: 18/518,071

(22) PCT Filed: May 24, 2021

(86) PCT No.: PCT/US2021/033830
§ 371 (c)(1),
(2) Date: Nov. 22, 2023

(87) PCT Pub. No.: WO2022/250644
PCT Pub. Date: Dec. 1, 2022

(65) Prior Publication Data

US 2025/0152443 A1 May 15, 2025

(51) Int. Cl.
*A61G 12/00* (2006.01)
*A61B 5/00* (2006.01)
*A61G 7/10* (2006.01)

(52) U.S. Cl.
CPC .......... *A61G 12/008* (2013.01); *A61B 5/0046* (2013.01); *A61G 7/1028* (2013.01); *A61B 2560/0437* (2013.01); *A61G 2210/50* (2013.01)

(58) Field of Classification Search
CPC .. A61G 7/1026; A61G 7/1028; A61G 12/008; A61G 2210/50; A61B 5/0046; A61B 2560/0437
See application file for complete search history.

(56) References Cited

U.S. PATENT DOCUMENTS 1,280,792 A * 10/1918 MacEachern ...... A61G 13/0009 5/430
5,121,512 A 6/1992 Kaufmann
(Continued)

FOREIGN PATENT DOCUMENTS

CN 104105467 A 10/2014
CN 204352073 U 5/2015
(Continued)

OTHER PUBLICATIONS

Office Action (Notification of Reasons for Refusal) issued Dec. 24, 2024, by the Japan Patent Office in corresponding Japanese Patent Application No. 2024-516341 and an English machine translation of the Office Action. (9 pages).
(Continued)

*Primary Examiner* — Craig M Schneider
(74) *Attorney, Agent, or Firm* — Buchanan Ingersoll & Rooney PC

(57) ABSTRACT

An air caddy operable within an MRI room and adjacent an MRI apparatus in the MRI room includes a base portion having at least one wheel positioned to selectively permit movement of the caddy relative to a floor. The base portion is movable between a mobile orientation in which the at least one wheel facilitates movement of the caddy relative to the floor and a stationary orientation in which the at least one wheel is prevented from facilitating movement of the caddy relative to the floor. An electric blower is coupled to the base portion and fixed to prevent movement of the electric blower relative to the caddy. The electric blower moves air when the
(Continued)

base portion is in the stationary orientation. The relative position of the blower to the MRI apparatus does not change when the blower moves air and when the base portion is in the stationary orientation.

27 Claims, 9 Drawing Sheets

(56) References Cited

U.S. PATENT DOCUMENTS

| | | | | |
|---|---|---|---|---|
| 6,119,292 | A * | 9/2000 | Haas | A61G 7/001<br>5/713 |
| 7,735,164 | B1 | 6/2010 | Patrick | |
| 8,276,222 | B1 | 10/2012 | Patrick | |
| 10,709,627 | B2 | 7/2020 | Herrschaft et al. | |
| 11,737,934 | B2 * | 8/2023 | Coppens | A61G 1/02<br>324/318 |
| 2003/0197340 | A1 | 10/2003 | Udall et al. | |
| 2013/0145549 | A1 | 6/2013 | Piegdon et al. | |
| 2017/0049646 | A1 | 2/2017 | Rigoni et al. | |
| 2018/0008495 | A1 | 1/2018 | Herrschaft et al. | |
| 2018/0296121 | A1 | 10/2018 | Coppens et al. | |

FOREIGN PATENT DOCUMENTS

| | | | | |
|---|---|---|---|---|
| EP | 0 262 592 | A2 | 4/1988 | |
| GB | 2287001 | A * | 9/1995 | A61G 13/06 |
| JP | 2688375 | B2 | 12/1997 | |
| JP | 2010-240059 | A | 10/2010 | |
| JP | 3200227 | U | 10/2015 | |
| JP | 2017-127472 | A | 7/2017 | |

OTHER PUBLICATIONS

Office Action (Communication pursuant to Article 94(3) EPC) issued Mar. 18, 2025, by the European Patent Office in corresponding European Patent Application No. 21 732 764.2-1113. (5 pages).

Notification Concerning Transmittal of the International Preliminary Report on Patentability (Forms PCT/IB/326 and PCT/IB/373) and the Written Opinion of the International Searching Authority (Form PCT/ISA/237) issued Dec. 7, 2023, by the International Bureau of WIPO in corresponding International Application No. PCT/US2021/033830. (9 pages).

International Search Report and Written Opinion for International Application No. PCT/US2021/033830, dated Feb. 24, 2022, 11 pages.

Office Action (The First Office Action) issued Mar. 6, 2026, by the National Intellectual Property Administration, P. R. China in corresponding Chinese Patent Application No. 202180098668.2 and an English translation of the Office Action. (20 pages).

* cited by examiner

MRI COMPATIBLE AIR MANAGEMENT SYSTEM

CROSS-REFERENCE TO RELATED APPLICATIONS

This application is a U.S. national phase patent application of PCT Patent Application No. PCT/US2021/033830, titled MRI COMPATIBLE AIR MANAGEMENT SYSTEM, filed May 24, 2021, the contents of which are incorporated herein by reference in its entirety for all purposes.

FIELD OF THE INVENTION

The present invention generally relates to air management systems, associated systems, and methods for moving air for use, for example, in conjunction with transporting patients and providing safe transfer of a patient from a patient trolley to a target modality during medical procedures or diagnostic determinations.

BACKGROUND OF THE INVENTION

Patient trolleys are used frequently in hospitals and treatment centers to safely transport patients to various locations within the facility. When the patient requires therapy or diagnostic imaging, the patient trolleys are used to deliver the patient in proximity to certain target modalities. Target modalities may include various patient support surfaces associated with machines, such as CT, MR, and PET, an operating table, a hospital bed, an OR table, a treatment machine, robotic surgical arms, etc. Patient trolleys are expected to safely transport a patient to and from various target modalities. Often these patients must be immobilized to maintain positional accuracy and consistency from one modality to the next.

In order to transfer a patient from the top surface of a patient trolley to the surface of a target modality, patient transfer devices are commonly used. For patients that are not ambulatory and are expected to remain lying down, including in supine, prone, or recumbent positions, patient trolley operators should transport the patient trolley to a location that is as close as possible to the surface of the target modality. Additional adjustments can be made by lifting or raising the elevation of the top surface of the patient trolley and transferring the patient using the patient transfer device by sliding the patient transfer device from the top surface of the patient trolley to the top surface of the target modality.

Patient transfer devices may require a supply of air to facilitate their operation. For example, a patient transfer device optionally includes an air bearing attached to the underside of the patient transfer device. A source of air may be coupled to the patient transfer device and configured to deliver air to the air bearing.

MRI environments in particular present obstacles to the use of a patient trolley and transfer device. Due to the tremendous strength of the magnetic field generated by an MRI machine, magnetic materials, such as ferromagnetic materials, can present a hazard in an MRI environment and therefore are carefully monitored and typically limited, complicating the construction of any device for use in and around the MRI machine. Accordingly, it is often necessary to prevent the introduction of an air supply into an MRI environment.

Thus, a need exists for improved air management systems that can be used for the movement of air within an MRI environment, for example to facilitate easier patient transfer to target modalities within an MRI environment. These and other needs are addressed by the air management system and associated systems and methods of the present invention.

SUMMARY OF THE INVENTION

According to an aspect of the invention, an air caddy operable within an MRI room and adjacent an MRI apparatus in the MRI room is provided. The caddy is configured for permitting continuous contact with a floor of the MRI room and movement along the floor of the MRI room. The caddy includes a base portion having at least one wheel positioned to selectively permit movement of the caddy relative to a floor, the base portion being movable between a mobile orientation in which the at least one wheel facilitates the movement of the caddy relative to the floor and a stationary orientation in which the at least one wheel is prevented from facilitating the movement of the caddy relative to the floor. The caddy also includes an electric blower coupled to the base portion of the caddy and fixed to prevent movement of the electric blower relative to the caddy, the electric blower being configured to move air when the base portion is in the stationary orientation, and the relative position of the blower to the MRI apparatus in the MRI room does not change when the blower moves air and when the base portion is in the stationary orientation, the electric blower being mounted such that the electric blower remains within a weaker portion of a magnetic field generated by the MRI apparatus in the MRI room, thereby reducing the effect of the magnetic field on the operation of the electric blower during use of the electric blower. The caddy is MR Compatible with a maximum magnetic attraction force less than or equal to 50 lbs force. The caddy is positionable adjacent the MRI apparatus within the MRI room and the magnetic field of the MRI apparatus does not interfere with the operation of the electric blower when the caddy is positioned adjacent the MRI apparatus, such that the electric blower operates while adjacent the MRI apparatus and while the magnetic field is generated by the MRI apparatus.

The caddy can be configured for movement of the electric blower relative to a patient transfer device that is configured for movement relative to a patient support, the electric blower being configured to move air to the patient transfer device. The patient transfer device can provide an air bearing, and the electric blower can be configured to move air to the air bearing.

The caddy can include at least two wheels positioned for movement of the caddy relative to the floor.

The caddy can be MR Compatible with a maximum magnetic attraction force less than or equal to 25 lbs force.

The caddy can include a battery for powering the electric blower. At least one of the battery and the electric blower can be located within a central region of the base portion.

The caddy can be configured such that the at least one wheel is positioned to contact the floor to permit movement of the caddy relative to the floor when the base portion is in the mobile orientation, and the at least one wheel being spaced from the floor to be prevented from facilitating the movement of the caddy relative to the floor when the base portion is positioned in the stationary orientation.

The caddy can be configured such that the at least one wheel can be locked to retain the caddy in the stationary orientation and unlocked to revert to the mobile orientation.

The base portion of the caddy can have a bottom surface comprising at least one floor-contacting surface positioned to elevate the at least one wheel from the floor when the base portion is in the stationary orientation.

The at least one wheel can be mounted to rotate about an axis that is fixed in position relative to the base portion of the caddy. A distance from the axis to the at least one floor-contacting surface of the base portion can be greater than a distance from the axis to a floor-contacting surface of the at least one wheel. The center of mass of the caddy is positioned relatively forward relative to the axis toward a front of the caddy in the stationary orientation, and the center of mass can be positioned relatively over the axis in the mobile orientation. The center of mass of the caddy can be positioned between the axis and the front of the caddy such that the caddy moves from the mobile orientation to the stationary orientation when released from the mobile orientation.

In the caddy, air can be movable by the electric blower to or from at least one of a patient transfer device, a patient bed, a wound care bed, a bed that provides alternating pressures, a surface designed for therapeutic applications, a surface designed for patient comfort, a skin protection surface, an air powered device, a vacuum cushion and a compression surface.

The electric blower of the caddy can be configured to be coupled to a patient transfer device for moving air to an air bearing of the patient transfer device.

A supplemental mass can be mounted to the caddy to provide a threshold mass. The supplemental mass can provide the threshold mass selected such that the caddy is prevented from leaving the continuous contact with the floor of the MRI room in response to a magnetic force of attraction generated by the MRI apparatus. The supplemental mass can be selected to overcome the magnetic force of attraction when the caddy is in the continuous contact with the floor of the MRI room and directly adjacent to the MRI apparatus when the MRI apparatus is operated to generate a magnetic field.

The supplemental mass can providing the threshold mass such that the caddy maintains a desired center of gravity. The supplemental mass can be positioned to maintain the center of gravity such that the caddy is biased to move toward the stationary orientation from the mobile orientation. The supplemental mass can be positioned to locate the center of gravity of the caddy forward relative to an axle of the at least one wheel. The supplemental mass optionally has no functionality other than establishing the threshold mass. The supplemental mass can be configured to both provide prevent the caddy from leaving the continuous contact with the floor of the MRI room in response to a magnetic force of attraction generated by the MRI apparatus and to maintain the center of gravity such that the caddy is biased to move toward the stationary orientation from the mobile orientation. The supplemental mass can be non-magnetic.

The caddy may include two or more wheels.

The caddy may include a handle mounted to the base portion to facilitate movement of the caddy.

According to another aspect of the invention, a method is provided for moving a patient relative to a bore of an MRI device using a patient transfer device. The method includes positioning a caddy proximate to the bore of the MRI device, the caddy being MR Compatible with a maximum magnetic attraction force less than or equal to 50 lbs force and including a base portion configured for movement relative to a floor, at least one wheel coupled to the base portion and positioned for movement of the base portion relative to the floor, and an electric blower, the electric blower being mounted such that the electric blower remains within a weaker portion of a magnetic field generated by the bore of the MRI device, thereby reducing the effect of the magnetic field on the operation of the electric blower during use of the electric blower. The method includes moving the base portion from a mobile orientation in which the at least one wheel facilitates the movement of the caddy relative to the floor to a stationary orientation in which the at least one wheel is prevented from facilitating the movement of the caddy relative to the floor; actuating the electric blower to move air to the patient transfer device, thereby moving air to or from the patient transfer device to facilitate movement of the patient, the electric blower operating while adjacent the bore of the MRI device and while the magnetic field is being generated by the bore of the MRI device; and moving the patient and the patient transfer device relative to the bore of the MRI device.

The method can include moving the patient and the patient transfer device relative to the patient support portion.

DETAILED DESCRIPTION OF THE INVENTION

Figure 1B:
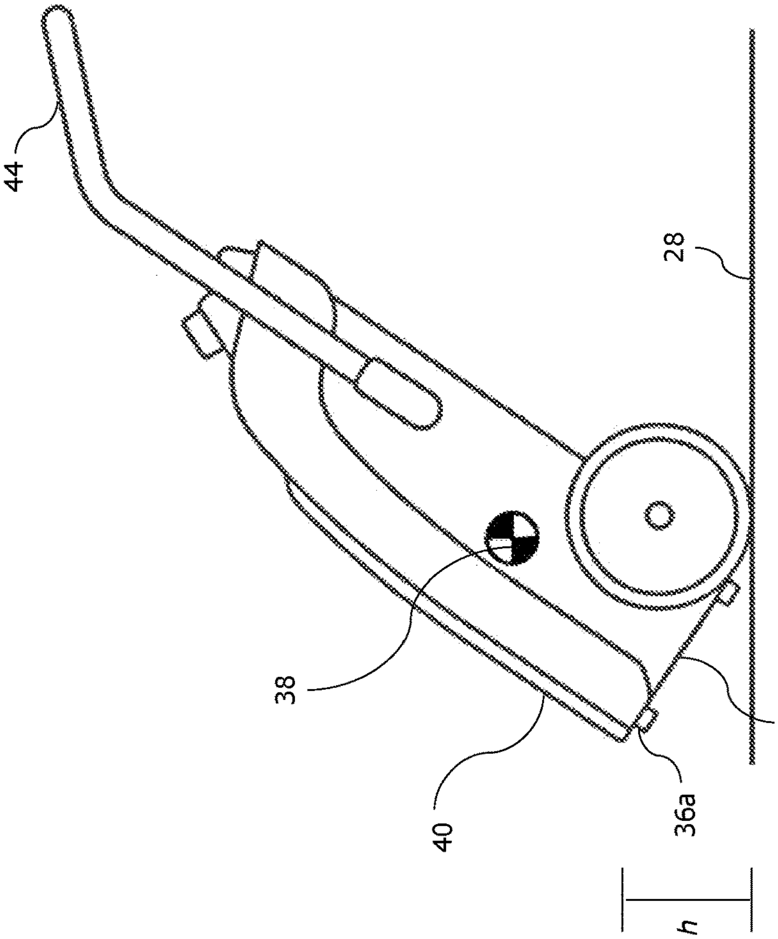
FIG. 1B is a side view of the embodiment of FIG. 1A, showing the embodiment in a mobile orientation.

The invention is described by reference to exemplary embodiments and variations of those embodiments. Although the invention is illustrated and described herein with reference to specific embodiments, the invention is not intended to be limited to the details shown and described. Rather, various modifications may be made in the details within the scope and range of equivalents of the claims and without departing from the invention.

According to one aspect of this invention, an air management system 10 is configured for use in an MRI environment, such as with an imaging system comprising an MRI machine 12, a target modality 14, a trolley system 16, and a patient transfer device 18 configured for movement relative to a patient support portion 20. The patient transfer device 18 optionally includes an air bearing (not shown) attached to the underside of the patient transfer device 18. The imaging system may be combined with an air management system 10, such as but not limited to a source of low pressure/high volume air coupled to the patient transfer device 18 and configured to deliver air to the air bearing. For example a low pressure/high volume air source 10 may be 0.1 to 5 PSI and 50 to 200 CFM. The air bearing can be of many designs as known to those skilled in the art, including but not limited to, a bladder, a cushion, etc. The air source 10 provides air flow to the air bearing and facilitates the transfer of a patient from a top surface of the trolley system 16 to a patient surface 22 of the target modality 14.

Motors 24 for the air management system 10, such as blowers used for the operation of patient transfer devices 18, may be made of magnetic materials and/or include electrically powered components. The magnetic field can disrupt the operation of the motors 24, and the magnetic materials can be attracted to the magnetic field of the MRI machine 12, thus threatening the safe operation of the transfer devices 18. This invention mitigates this risk through placement of the motor 24 and other components to ensure their proper functioning and to reduce magnetic attraction in the MRI environment. As a result, the systems 10 according to the embodiments described herein may be compatible with the MRI environment. As used herein throughout the specification and the claims, the term "MR Compatible" refers to the magnetic attraction force of the air management system 10 and the operability of one or more electric motors 24 of the air management system 10 as determined by the MR Compatibility Test Procedure described in the Examples section below.

Regarding the magnetic attraction force of the air management system 10, it has been surprisingly discovered that an air management system 10 can be provided according to aspects of this invention while still having a magnetic attraction force that renders it suitable for use in an MRI environment such as an MRI room. According to embodiments of the invention, the maximum magnetic attraction force is less than or equal to 50 lbs force, and more preferably less than or equal to 25 lbs force, as determined by the MR Compatibility Test Procedure described in the Examples section below.

Regarding the operability of one or more electric motors 24 of the air management system 10, it has been surprisingly discovered that an air management system 10 having one or more electric motors 24 can be provided according to aspects of this invention while still remaining operable in an MRI environment such as an MRI room. According to embodiments of the invention, operability of one or more electric motors 24 of the air management system 10 is maintained, as determined by the MR Compatibility Test Procedure described in the Examples section below.

Previously, portable blowers have been provided with long hoses (not shown) for the patient transfer device 18, so that the blower motor can remain outside of the MRI environment (in practice, outside the MRI room) while the patient is transferred to avoid an unsafe situation. However, it is preferred to avoid the need for such a blower arrangement with long hoses and electrical cords (not shown).

By affixing a blower 24 to an air management system 10 according to aspects of this invention, the location and orientation of the blower 24 relative to the MRI machine 12 is controlled such that its function is not impeded. In addition, it has been discovered that the air management system 10, which is composed primarily of non-magnetic materials, is of sufficient mass that provides an anchoring function for the blower 24 and other features containing magnetic components. This prevents the blower 24 from being separated intentionally or unintentionally from the floor surface on which is rests or from being dangerously pulled toward and into the MRI machine 12. Providing a battery power source 26 eliminates the need for electrical cords thereby enabling the unit to be self-contained. Tripping hazards and MRI interference from the electrical cord can also be avoided.

Additionally, it is desirable to optionally use a motor 24, such as a vacuum pump motor in an MRI environment. Such vacuum pump motors are useful for, among other things, forming vacuum cushions for use during MR imaging. According to aspects of this invention, one or more vacuum pump motors is provided by the air management system 10.

According to an aspect of the invention, the air management system 10, such as an air caddy **10*a* operable within an MRI room and adjacent an MRI apparatus 12 in the MRI room, is provided. The caddy 10*a* is configured for permitting continuous contact with a floor 28 of the MRI room and movement along the floor 28 of the MRI room. The caddy 10*a* includes a base portion 32 having at least one wheel 34 positioned to selectively permit movement of the caddy 10*a* relative to the floor 28, the base portion 32 being movable between a mobile orientation in which the at least one wheel 34 facilitates the movement of the caddy 10*a* relative to the floor 28 and a stationary orientation in which the at least one wheel 34 is prevented from facilitating the movement of the caddy 10*a* relative to the floor 28. The caddy 10*a* also includes an electric blower 24 coupled to the base portion 32 of the caddy 10*a* and fixed to prevent movement of the electric blower 24 relative to the caddy 10*a*, the electric blower 24 being configured to move air when the base portion 32 is in the stationary orientation, and the relative position of the blower 24 to the MRI apparatus 12 in the MRI room does not change when the blower 24 moves air and when the base portion 32 is in the stationary orientation, the electric blower 24 being mounted such that the electric blower 24 remains within a weaker portion of a magnetic field generated by the MRI apparatus 12 in the MRI room, thereby reducing the effect of the magnetic field on the operation of the electric blower 24 during use of the electric blower 24. The caddy 10*a* is MR Compatible with a maximum magnetic attraction force less than or equal to 50 lbs force. The caddy 10*a* is positionable adjacent the MRI apparatus 12 within the MRI room and the magnetic field of the MRI apparatus 12 does not interfere with the operation of the electric blower 24 when the caddy 10*a* is positioned adjacent the MRI apparatus 12, such that the electric blower 24 operates while adjacent the MRI apparatus 12 and while the magnetic field is generated by the MRI apparatus 12**.

The caddy **10*a* can be configured for movement of the electric blower 24 relative to a patient transfer device 18 that is configured for movement relative to a patient support 20, the electric blower 24 being configured to move air to the patient transfer device 18. The patient transfer device 18 can provide an air bearing (not shown), which may be attached to the underside of the patient transfer device 18, and the electric blower 24** can be configured to move air to the air bearing.

The caddy **10*a* can include at least two wheels 34 positioned for movement of the caddy 10*a* relative to the floor 28**.

The caddy 10*a* can be MR Compatible with a maximum magnetic attraction force less than or equal to 25 lbs force.

The caddy 10*a* can include a battery 26 for powering the electric blower 24. At least one of the battery 26 and the electric blower 24 can be located within a central region of the base portion 32.

The caddy 10*a* can be configured such that the at least one wheel 34 is positioned to contact the floor 28 to permit movement of the caddy 10*a* relative to the floor 28 when the base portion 32 is in the mobile orientation, and the at least one wheel 34 being spaced from the floor 28 to be prevented from facilitating the movement of the caddy 10*a* relative to the floor 28 when the base portion 32 is positioned in the stationary orientation.

The caddy 10*a* can be configured such that the at least one wheel 34 can be locked to retain the caddy 10*a* in the stationary orientation and unlocked to revert to the mobile orientation.

The base portion 32 of the caddy 10*a* can have a bottom surface 36 comprising at least one floor-contacting surface 36*a* positioned to elevate the at least one wheel 34 from the floor when the base portion 32 is in the stationary orientation.

The at least one wheel 34 can be mounted to rotate about an axis that is fixed in position relative to the base portion 32 of the caddy 10*a*. A distance from the axis to the at least one floor-contacting surface 36*a* of the base portion 32 can be greater than a distance from the axis to a floor-contacting surface 36*a* of the at least one wheel 34. The center of mass 38 of the caddy 10*a* is positioned relatively forward relative to the axis toward a front 40 of the caddy 10*a* in the stationary orientation, and the center of mass 38 can be positioned relatively over the axis in the mobile orientation. The center of mass 38 of the caddy 10*a* can be positioned between the axis and the front 40 of the caddy 10*a*, such that the caddy 10*a* moves from the mobile orientation to the stationary orientation when released from the mobile orientation.

In the caddy 10*a*, air can be movable by the electric blower 24 to or from at least one of a patient transfer device 18, a patient bed, a wound care bed, a bed that provides alternating pressures, a surface designed for therapeutic applications, a surface designed for patient comfort, a skin protection surface, an air powered device, a vacuum cushion and a compression surface.

The electric blower 24 of the caddy 10*a* can be configured to be coupled to a patient transfer device 18 for moving air to an air bearing (not shown) attached to the underside of the patient transfer device 18.

A supplemental mass 42 can be mounted to the caddy 10*a* to provide a threshold mass. The supplemental mass 42 can provide the threshold mass selected such that the caddy 10*a* is prevented from leaving the continuous contact with the floor 28 of the MRI room in response to a magnetic force of attraction generated by the MRI apparatus 12. The supplemental mass 42 can be selected to overcome the magnetic force of attraction when the caddy 10*a* is in the continuous contact with the floor 28 of the MRI room and directly adjacent to the MRI apparatus 12 when the MRI apparatus 12 is operated to generate a magnetic field.

The supplemental mass 42 can provide the threshold mass such that the caddy 10*a* maintains a desired center of gravity 38. The supplemental mass 42 can be positioned to maintain the center of gravity 38 such that the caddy 10*a* is biased to move toward the stationary orientation from the mobile orientation. The supplemental mass 42 can be positioned to locate the center of gravity 38 of the caddy 10*a* forward relative to an axle of the at least one wheel 34. The supplemental mass 42 optionally has no functionality other than establishing the threshold mass. The supplemental mass 42 can be configured to both provide prevent the caddy 10*a* from leaving the continuous contact with the floor 28 of the MRI room in response to a magnetic force of attraction generated by the MRI apparatus 12 and to maintain the center of gravity 38 such that the caddy 10*a* is biased to move toward the stationary orientation from the mobile orientation. The supplemental mass 42 can be non-magnetic.

The caddy 10*a* may include two or more wheels 34.

The caddy 10*a* may include a handle 44 mounted to the base portion 32 to facilitate movement of the caddy 10*a*.

Figure 4:
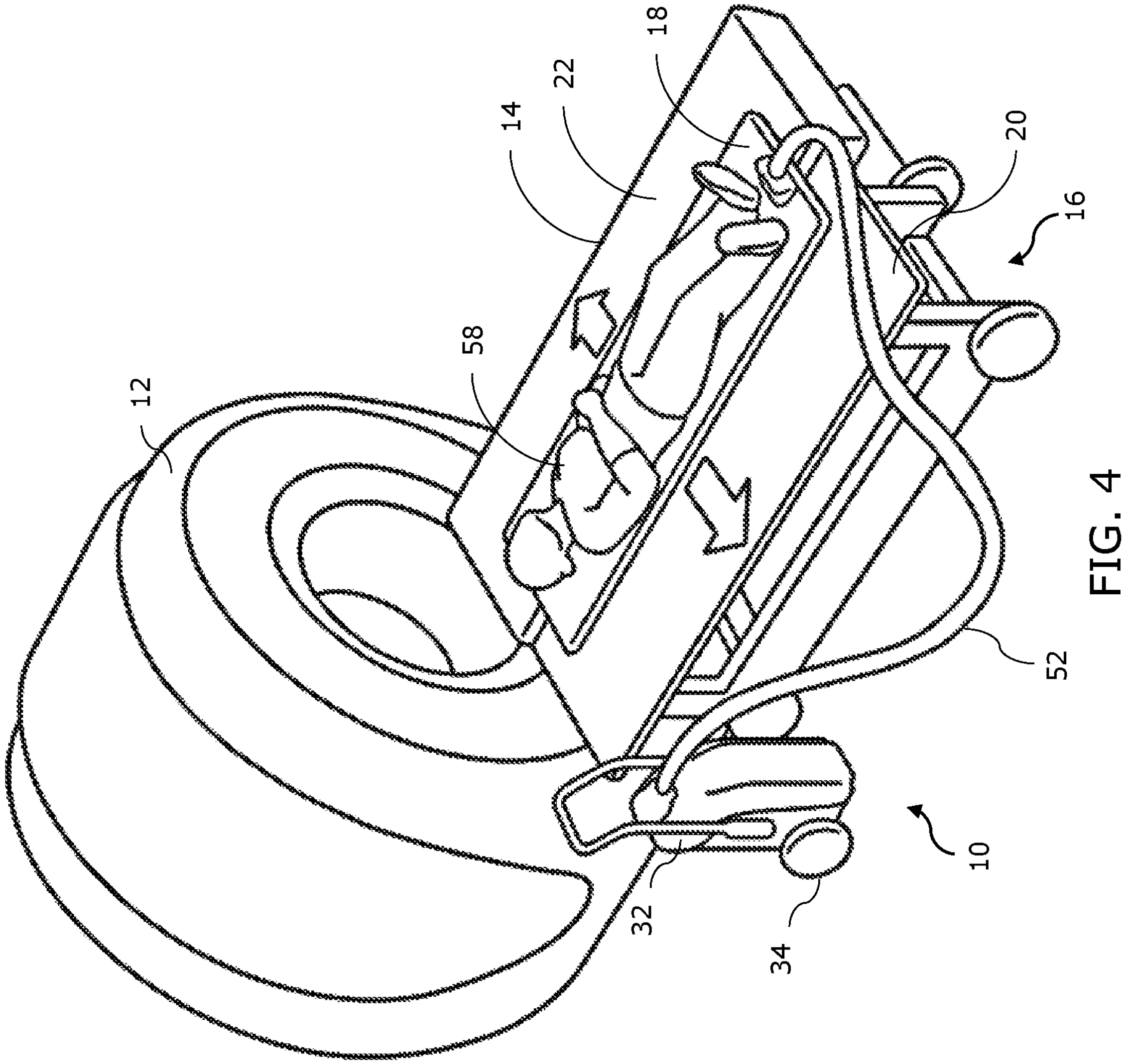
FIG. 4 shows the embodiment of FIG. 1A, in use during a lateral transfer situation with a transfer device, the patient support of the target modality, and a separate patient support.

A patient trolley 16 is illustrated in FIG. 4 within an MRI environment. The patient trolley 16 is adjacent to an MRI table 46 and is located near the bore of an MRI machine 12. The patient trolley 16 includes a patient transfer device 18 to facilitate transfer from the top of the patient trolley 16 to the patient support surface 48 of the MRI table 46.

Figure 5:
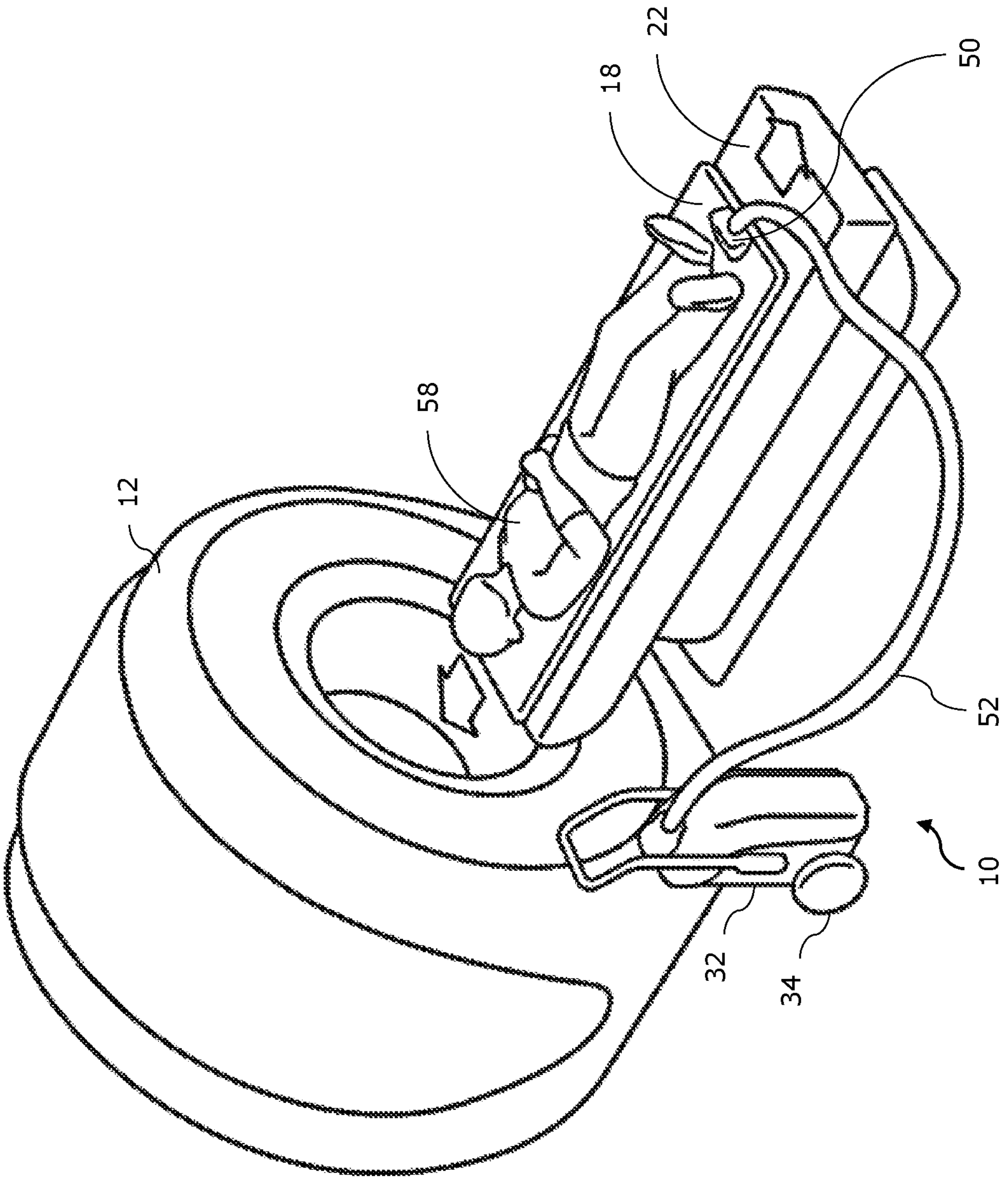
FIG. 5 shows the embodiment of FIG. 1A, in use during a longitudinal transfer situation, with a transfer device and the patient support of the target modality.

Transfer of a patient from the patient trolley 16 to the MRI table 46 is facilitated by delivering air to an air bearing, which may be attached to the underside of the patient transfer device 18, by using an air management system according to aspects of this invention. This air bearing reduces the friction between the patient transfer device 18 and the surface, such as surface 22, along which it travels (FIG. 5).

The magnetic field strength of most commercial MRI machines 12 used for diagnostic imaging for humans is within the range of 0.35 to 3 Tesla. However, this rating only describes the maximum strength of the magnetic field within the bore of the MRI machine 12. As illustrated in the schematic illustration of FIG. 2, the magnetic field strength of the MRI machine 12 decreases with distance. The force exerted on any magnetic components is related to the field strength where the components are located. Because portions of the air management system 10 will be close to the bore of the MRI machine 12 when the patient transfer device 18 is in position to transfer the patient, it is preferred that non-magnetic materials are used to manufacture the air management system 10, particularly the top and leading portions of the air management system 10, which will be in close proximity to the MRI machine 12.

Due to physical property requirements or cost demands, it may be impractical to include components made solely from non-magnetic materials. In order to further minimize the potential effects of the magnetic field from the MRI machine 12 on the air management system 10, the components remain fixed or at least are positioned near the base of the air management system 10. Assuming that the MRI machine 12 has the magnetic field profile of a typical 3T machine (such as the magnetic field profile illustrated in FIG. 2), the base portion 32 of the air management system 10 will be exposed to magnetic field strengths generally no greater than 200 mT due to the location of the base portion 32 relative to the MRI machine 12.

The patient transfer device 18 includes a hose connector 50 (FIG. 5) to receive one end of a hose 52. The hose 52 preferably has two sections. The top section has two opposing ends in which one end is connected to the hose connecter 50 of the patient transfer device 18 and the opposite end is connected to the air management system 10.

While various blowers 24 can be utilized in the air management system 10, one exemplary blower 24 is available from AMETEK Corp. (e.g., AMETEK Lamb Electric 116157-00). Further options and alternatives and details are provided below. As explained above, it is preferred that components of the air management system 10, such as motors, a blower, a control unit, and/or a battery pack, are mounted to the base portion 32 of the air management system 10 to minimize the effect of the magnetic field of the MRI machine 12 on the operation of the motors 24 during use of the blower 24 during a patient transfer. In one embodiment, the blower 24 can optionally be positioned in a weaker portion of the magnetic field. For example, mounting the blower 24 closer to the bottom surface 36 of the air management system 10 minimizes the potential for interference by the magnetic forces on the blower 24. More preferably, the components in the base 52 of the patient trolley 16 are mounted, such that the elevation of one or more of these components is fixed relative to the floor 28 upon which the air management system 10 travels. Alternatively, the elevational travel of the components can be permitted and limited. According to various embodiments of the present invention, it is preferred to include a blower 24 that is firmly attached to the air management system 10, i.e. not separately portable. A separately portable blower is likely to contain magnetic material and when not firmly attached to the air management system 10 can pose a severe risk of becoming a projectile in an MRI environment.

It is possible for the magnetic forces generated by the MRI machine to overcome the force of gravity or the force holding such a blower 24 in position because the mass of the blower 24 is not sufficient to resist the attraction force generated by the MRI machine 12. If the blower 24 is not maintained at a safe distance from the MRI machine 12, the blower 24 may be attracted by and pulled into the bore of the MRI machine 12. This is a potentially dangerous occurrence because the blower 24 may strike and injure an operator or patient that is also in the vicinity of the MRI machine 12. It may also damage the MRI machine 12 or the blower 24 itself. Previously, blowers 24 have been placed outside the room in which the MRI machine 12 is located to mitigate this risk.

Therefore, it is preferable that various embodiments of the air management system 10 according to the present invention include a blower 24 that is fixed in location relative to the air management system 10, preferably at a position that will remain at a distance from the MRI machine 12 at which the MRI will not interfere with the functioning of the blower 24. Furthermore, it has been discovered that the configuration of the blower's 24 location on the air management system 10 according to the various embodiments of the present invention reduces the magnetic attraction force created by the magnetic components of the blower 24.

Similarly, if the blower 24 for the patient transfer device 18 and the motor or motors (not shown) used to operate the actuator (not shown) of the patient trolley 16 include electric motors, the strength of the MRI machine 12 also has the potential to disrupt the operation of the motors. As understood by those of skill in the art, electric motors typically utilize magnetic fields to produce mechanical motion, providing a driving mechanism. These motors can contain both electromagnets and fixed magnets. These electric motors may be disrupted by an external magnetic field. Therefore, the configuration of the motor and blower 24 in the base of the air management system 10 according to various embodiments of the present invention are necessary to ensure proper functioning of delivering air to the patient transfer device 18.

As explained above, the blower 24 is preferably mounted in the base 32 of the air management system 10 sufficiently far away from the bore of the MRI machine 12, such that the magnetic field of the MRI does not interfere with the operation of the blower 24.

According to another aspect of the invention, a method is provided for moving a patient relative to a bore of an MRI device 12 using a patient transfer device 18. The method includes positioning a caddy **10*a* proximate to the bore of the MRI device, the caddy 10*a* being MR Compatible with a maximum magnetic attraction force less than or equal to 50 lbs force and including a base portion 32 configured for movement relative to a floor 28, at least one wheel 34 coupled to the base portion 32 and positioned for movement of the base portion 32 relative to the floor 28, and an electric blower 24, the electric blower 24 being mounted such that the electric blower 24 remains within a weaker portion of a magnetic field generated by the bore of the MRI device 12, thereby reducing the effect of the magnetic field on the operation of the electric blower 24 during use of the electric blower 24. The method includes moving the base portion 32 from a mobile orientation in which the at least one wheel 34 facilitates the movement of the caddy 10*a* relative to the floor 28 to a stationary orientation in which the at least one wheel 34 is prevented from facilitating the movement of the caddy 10*a* relative to the floor 28; actuating the electric blower 24 to move air to the patient transfer device 18, thereby moving air to or from the patient transfer device 18 to facilitate movement of the patient, the electric blower 24 operating while adjacent the bore of the MRI device 12 and while the magnetic field is being generated by the bore of the MRI device 12; and moving the patient and the patient transfer device 18 relative to the bore of the MRI device 12**.

The method can include moving the patient and the patient transfer device 18 relative to the patient support portion 20.

Figure 1A:
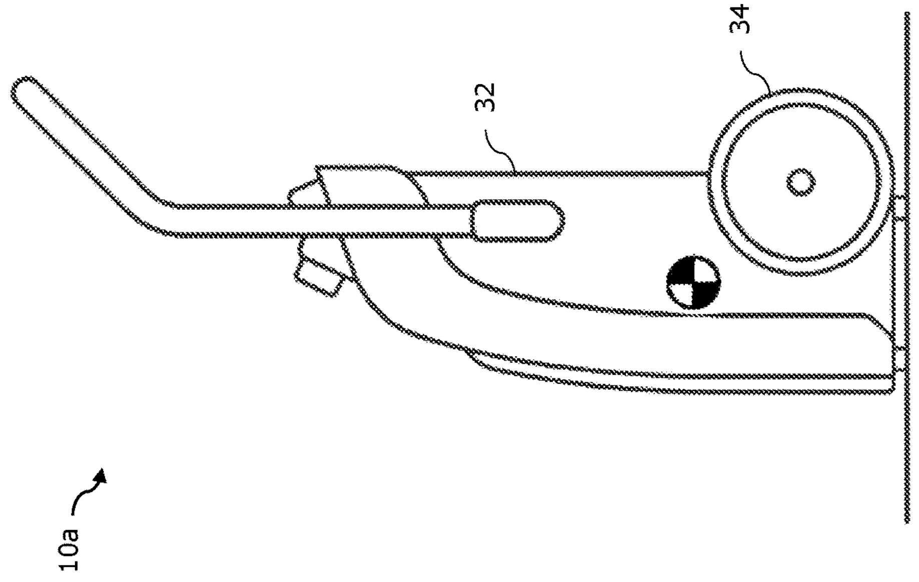
FIG. 1A is a side view of another embodiment of the air management system of the present invention, showing the embodiment in a stationary orientation.

In an embodiment of the present invention and referring generally to FIGS. 4-5, an air management system 10 such as air caddy **10*a* is configured to move air within an MRI room and adjacent an MRI apparatus 12 in the MRI room. The caddy 10*a* comprises a base portion 32, which includes at least one wheel 34 that is positioned to selectively permit movement of the caddy 10*a* relative to a floor 28. Further, the base portion 32 is movable between a mobile orientation (as shown in FIG. 1B) and a stationary orientation (as shown in FIG. 1A). In the mobile orientation, the at least one wheel 34 of the base portion 32 facilitates movement of the caddy 10*a* relative to the floor 28. In the stationary orientation, the at least one wheel 34 of the base portion 32 is prevented from facilitating the movement of the caddy 10*a* relative to the floor 28**.

The caddy **10*a* further includes an electric blower 24 coupled to the base portion 32. The electric blower 24 is fixed and is configured as being prevented from movement relative to the base portion 32. When the base portion 32 is in the stationary position, the electric blower 24 is configured to move air. Notably, when the electric blower 24 moves air, the position of the blower 24 relative to the MRI apparatus 12 in the MRI room does not change. Conventionally, such electric blowers 24 are configured to convey air from one side of the blower 24 to another. In this way, such blowers 24 can be configured such that they can either deliver or withdraw air, for example, connecting an air delivery means to either an inlet or an outlet. As such, it would be understood by someone skilled in the art that a blower 24 can act in both the mode of providing pressure and/or vacuum to a target device. In addition, it would be understood that electric blowers 24 of this type can include one or more of the following: centrifugal blowers, piston blowers, rotary vane vacuum pumps, diaphragm, liquid rings, venturi systems, screw pumps, and other blower means known to a person having ordinary skill in the art. Depending on the application, one might incorporate multiple blowers 24 or multiple types of blowers 24 or one might connect to multiple sides of a single blower 24** to selectively configure the system to either deliver or withdraw air, for instance utilizing a valve or switch or other means known to a person having ordinary skill in the art.

An electric blower, such as electric blower 24 of caddy 10*a*, that is configured to withdraw air may also be used to drive a fluid management system. For example, the electric blower 24 may be configured for use during various interventions to aspirate items such as bodily fluids, air, bone fragments, and foreign objects. Such fluid management systems include, but are not limited to, suction devices, aspirators, drains, and other systems known to one having skill in the art. Typical commercially available examples of such fluid management systems include, for example, the DeVilbiss Vacu-Aide® Compact Suction Unit and the Getinge Atrium Express Dry Seal Chest Drain. The blower 24 can be configured for use with other applications and devices.

Various models of pumps can be used as an electric blower 24 of the caddy. For example, a Gast Vacuum Pump, such as Gast Model No. LAA-V103-NQ (part number RTD764) can be used. Also, a Gardner Denver Thomas Pump, such as Gardner Model No. G 08-T (part number 50238) can be used. Other pumps can be employed as well.

Figure 2:
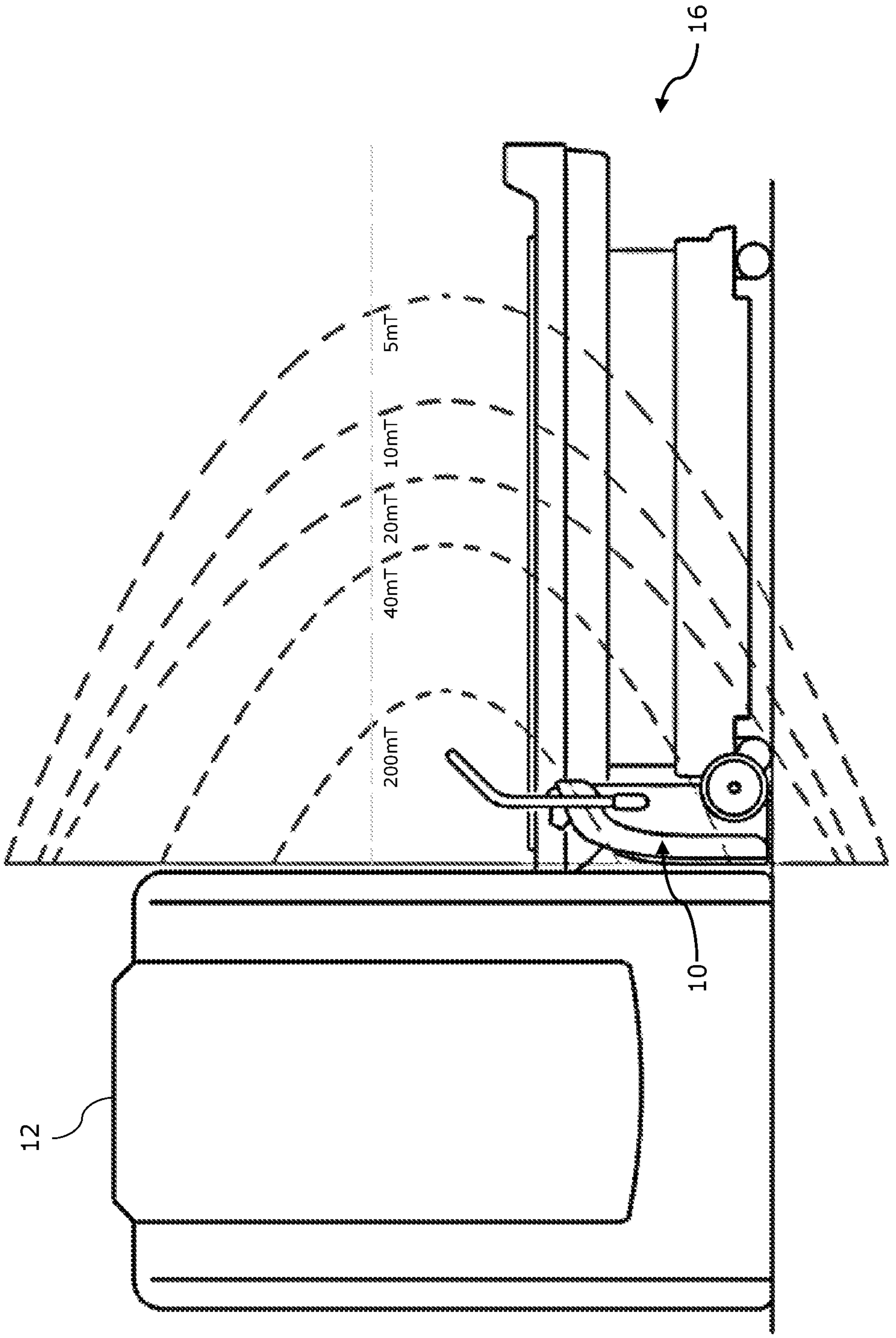
FIG. 2 is a side view of the embodiment of FIG. 1A within a magnetic field of an MRI machine.

As illustrated in the schematic illustration of FIG. 2, a magnetic field strength of the MRI apparatus 12 decreases with distance. To minimize the potential effects of the magnetic field generated by the MRI apparatus 12, the electric blower 24 remained in a fixed position relative to the MRI apparatus 12 and is at least positioned near the base of the MRI apparatus 12. In particular, the electric blower 24 is positioned such that the electric blower 24 remains within a relatively weaker portion of the magnetic field generated by the MRI apparatus 12 (such as the magnetic field profile illustrated in FIG. 2) in the MRI room, thereby reducing the effect of the magnetic field on the operation of the electric blower 24 during use of the electric blower 24. This way, the caddy 10*a* is positionable adjacent to the MRI apparatus 12 within the MRI room and the magnetic field of the MRI apparatus 12 does not interfere with the operation of the electric blower 24 in such a position. In other words, the electric blower 24 is functional and configured to operate while adjacent the MRI apparatus 12 and while the magnetic field is generated by the MRI apparatus 12. Specifically, the caddy 10*a* is configured to be MR Compatible with a maximum magnetic attraction force less than or equal to 50 lbs force.

As a non-limiting example, the caddy is a caddy 10*a*. The caddy 10*a* is operable to move the electric blower 24 relative to a patient transfer device 18 (FIG. 4). The patient transfer device 18 has an air bearing (not shown) attached to the underside of the patient transfer device 18, which can be coupled to the electric blower 24 configured to move air, such as deliver or withdraw air, for facilitating patient transfers. The patient transfers may involve movement of the patient transfer device 18 relative to a patient support 20 and operation of the electric blower 24 to move air to or from the patient transfer device 18. Although the electric blower 24 is illustrated to move air to or from the patient transfer device 18, as illustrated in FIGS. 4-5, it should be understood that the electric blower 24 can be configured to move air to or from at least one of the patient transfer device 18, a patient bed, a wound care bed, a bed that provides alternating pressures, a surface designed for therapeutic applications, a surface designed for patient comfort, a skin protection surface, an air powered device, a vacuum cushion, and a compression surface.

As noted above, the electric blower 24 may be configured for use during various interventions to aspirate items such as bodily fluids, air, bone fragments, and foreign objects.

Figure 3B:
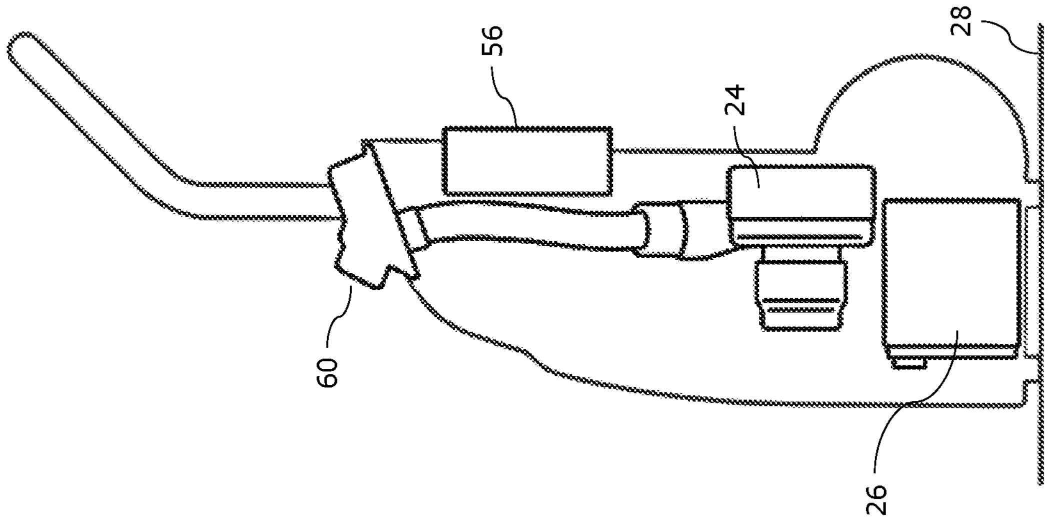
FIG. 3B shows a schematic side view of the embodiment of FIG. 3A, showing certain components of the air management system.
Figure 3A:
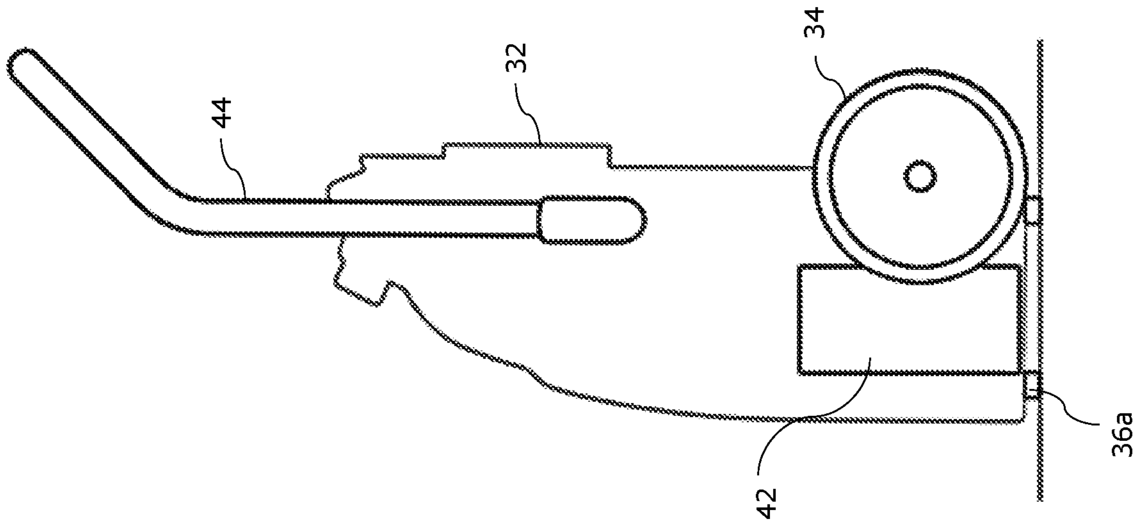
FIG. 3A shows a schematic side view of the embodiment of FIG. 1A, showing certain components of the air management system.

Referring now to FIGS. 1A-1C and 3A-3B, the caddy 10*a* comprises the base portion 32, to which is coupled the electric blower 24 configured to move air, such as deliver or withdraw air. As seen in FIG. 3B, the base portion 32 includes a battery 26 configured to power the electric blower 24 and a bottom surface 36 comprising a floor-contacting surface 36*a*.

Furthermore, a magnetic field indicator 56 (FIG. 3B) may be mounted to the base portion 32 to indicate when the magnetic field sensed by the magnetic field indicator 56 is above a threshold magnetic field strength. The magnetic field indicator 56 (FIG. 3B) may provide feedback, such as visual feedback (e.g. an LCD display screen, LED indicators), audio feedback (e.g., a speaker, a buzzer), or tactile feedback (e.g., haptic actuators), or any other means for providing feedback known to a person of ordinary skill in the art. Although FIG. 3B shows the magnetic field indicator 56 as being mounted to the base portion 32, it may also be mounted to a handle 44 (discussed further below). The magnetic field indicator 56 may be incorporated for additional user and safety considerations in the event that the caddy 10*a* is used in magnetic fields of unknown field strengths or to provide additional or redundant levels of safety.

Accordingly, in one embodiment of the caddy, a magnetic field indicator and/or sensor 56 can be included in the caddy 10*a* to provide an indication when the magnetic field exceeds a predetermined magnitude. This can provide a signal when the caddy 10*a* approaches or enters an area of selected high magnetic field, as noted above. For example, a Kopp Development Gauss Alert, such as Model 501-100 (100 Guass) (Part No. 9957-A-01828-B) or Model 501-30 (30 Gauss) (Part No. 9957-A-01790-B) can be employed.

In addition, the base portion 32 includes an inlet 60, such as a hose inlet (FIG. 3B), for receiving an end portion of a flexible hose or tube 52 (FIGS. 4-5). Correspondingly, the opposite end portion of the flexible hose or tube 52 is in communication with a portion of the patient transfer device 18 (FIG. 4-5) or the air bearing (not shown), which may be attached to or associated with the underside of the patient transfer device 18, thereby forming an air passageway between the electric blower 24 and the patient transfer device 18 or the air bearing (not shown). In other words, the electric blower 24 moves air to or from the air bearing (not shown) or the patient transfer device 18 via the flexible hose or tube 52.

As seen in FIG. 3B, the blower 24 is in a fixed position within the caddy 10*a*, such that the electric blower 24 is prevented from movement relative to the caddy 10*a*. Preferably, the blower 24 is positioned in a central or lower region of the base portion 32. Additionally or optionally, the battery 26 is positioned in the central region of the base portion 32. Further, the blower 24 is also in a fixed position relative to the MRI apparatus 12 when the blower 24 is operational and moves air.

As illustrated in FIGS. 2 and 3B, the electric blower 24 is positioned within the caddy 10*a*, such that the blower 24 remains within a relatively weaker portion of the magnetic field generated by the MRI apparatus 12. As an advantage of this, the electric blower 24 will operate when the caddy 10*a* is adjacent to the MRI apparatus 12 and while the MRI apparatus 12 generates the magnetic field.

This advantageous positioning reduces the effects of the magnetic field (such as the magnetic field profile illustrated in FIG. 2) on the operation of the electric blower 24. This can be partially demonstrated by the magnetic force of attraction on the caddy 10*a*. In a preferred embodiment, the magnetic force of attraction on the caddy 10*a* is less than 50 pounds of force. In a further preferred embodiment, the magnetic force of attraction on the caddy 10*a* is less than 25 pounds of force. This is measured using the MR Compatibility Test Procedure: Caddy Embodiment, as described further below.

As illustrated in FIG. 1A, the base portion 32 may include a non-magnetic supplemental mass 42 mounted to the base portion 32 to increase the mass of the air management system 10 to a threshold mass. It should be understood, however, that the threshold mass may be reached without the use of the non-magnetic supplemental mass 42, such that the caddy 10*a* and the components therein have sufficient total mass to reach the threshold mass.

According to a preferred embodiment of the invention, a non-magnetic mass, such as supplemental mass 42, is provided to accomplish dual functionalities. Specifically, according to a first functionality in this embodiment, the non-magnetic supplemental mass 42 provides a threshold mass such that the caddy 10*a* does not or cannot leave the floor 28 in response to a magnetic force of attraction. For example, the non-magnetic supplemental mass 42 can be selected to overcome a magnetic force of attraction even when the caddy 10*a* is on the floor in an MRI room and directly adjacent to the MRI apparatus 12 when the MRI apparatus 12 is operating to generate a magnetic field.

According to a second functionality in this embodiment, a non-magnetic supplemental mass, such as mass 42, also provides a threshold mass such that the caddy 10*a* has a center of gravity 38 maintained in a desired location. For example, threshold mass also impacts the center of gravity 38 of the caddy 10*a*, moving the center of gravity forward so that the caddy 10*a* is biased to move toward the stationary orientation from the mobile orientation, as described elsewhere in greater detail. Accordingly, for example, the weight of the mass 42 and the position of the mass 42 are selected in this embodiment to locate the center of gravity 38 forward on the caddy 10*a* relative to the axle of a wheel or wheels 34, or relative to another reference point.

The non-magnetic supplemental mass 42 may have no functionality other than one or more of the functions described above. For example, it may only serve the first functionality (threshold mass) and/or the second functionality (center of gravity). Alternatively, the non-magnetic supplemental mass 42 may be at least one component of the caddy 10*a* that serves at least one additional function (e.g., the function of a battery, an instrument, a frame, a housing, or other component of the caddy 10*a*). For example, the supplement mass 42 can be integrated into or be part of one or more functional components of the caddy 10*a*. The supplemental mass 42 may advantageously be non-magnetic.

Still further, the base portion 32 additionally has the at least one wheel 34 positioned to selectively permit movement of the caddy 10*a* relative to the floor 28. Preferably, the at least one wheel 34 includes two wheels. The base portion 32 of the caddy 10*a* is movable between two orientations, the mobile orientation (FIGS. 1B, 3B) and the stationary orientation (FIGS. 1A, 3A), via the at least one wheel 34. In the stationary orientation, the at least one floor-contacting surface 36*a* of the base portion 32 is adjacent or makes contact with the floor 28. In the mobile orientation, the at least one floor-contacting surface 36*a* of the base portion 32 is spaced or raised a distance or height, h, away from the floor 28 and a portion of the at least one wheel 34 is in contact with the floor 28 (FIG. 1B). Accordingly, the at least one wheel 34 facilitates movement of the caddy 10*a* across the floor 28 in any direction, when the caddy 10*a* is in the mobile orientation.

In the stationary orientation, the at least one wheel 34 is prevented from facilitating movement of the caddy 10*a* across the floor 28. This may be accomplished in a variety of ways known to a person having ordinary skill in the art, such as powered or manual brakes, wheel locks, and other mechanical or electrical means for inhibiting motion. Preferably, the prevention of movement of the at least one wheel 34 is accomplished by positioning the at least one wheel 34 such that it contacts the floor 28 when the caddy 10*a* is in the mobile orientation, but the at least one wheel 34 does not contact the floor 28 when the caddy 10*a* is in the stationary orientation. Stated differently, the at least one wheel 34 is elevated at a distance d (as seen in FIG. 12) relative to the floor 28, and thus the at least one wheel 34 is prevented from facilitating movement of the caddy 10*a* relative to the floor 28 in the stationary orientation.

Figure 6:
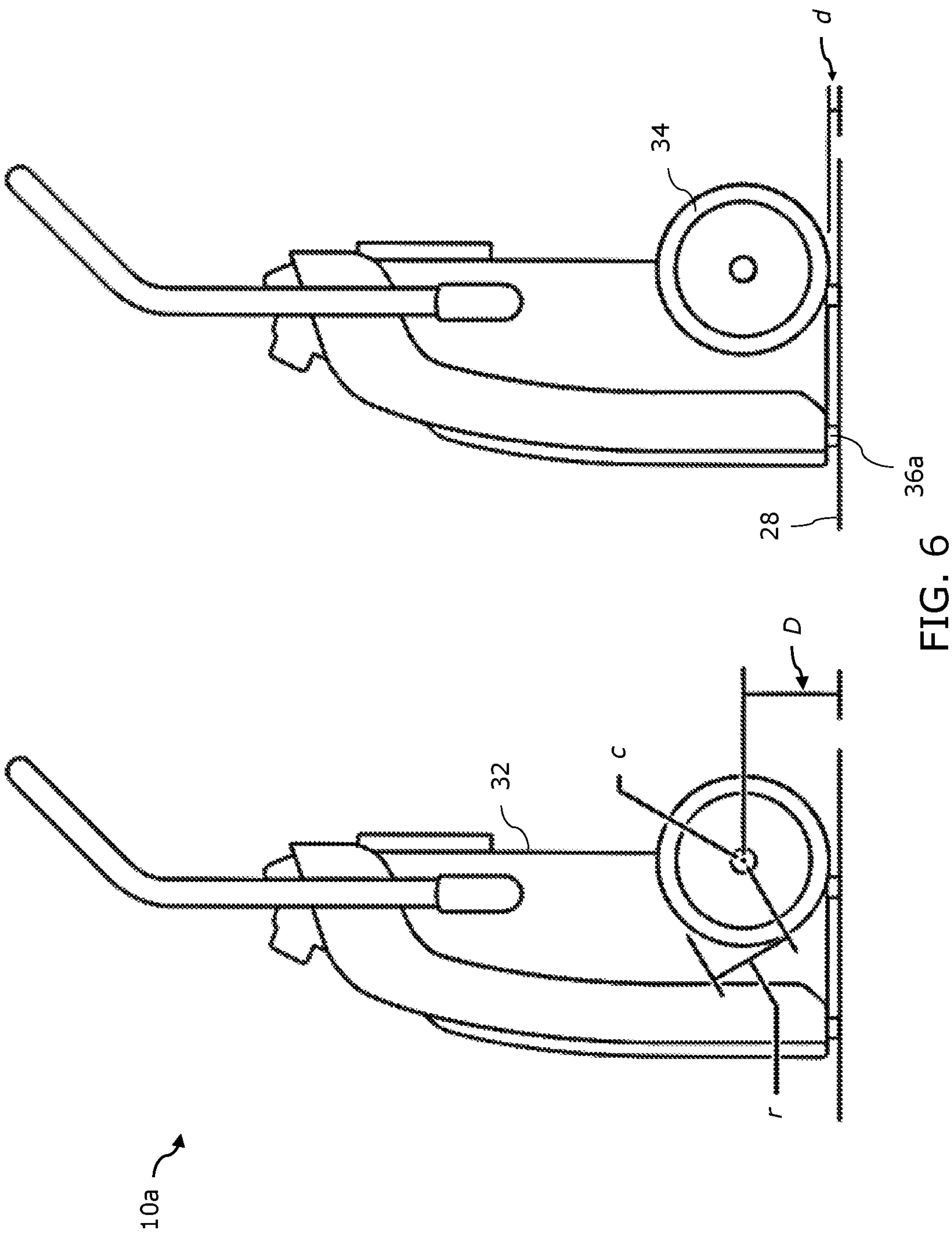
FIG. 6 shows a side view the embodiment of FIG. 1A, showing various distance relationships of the at least one wheel, the base portion, and the floor.

In a further preferred embodiment, as shown in FIG. 6, the at least one wheel 24 is mounted to the base portion 32, such that it is possible to select between the mobile and stationary orientations by changing the angle or tilting the caddy 10*a* about an axis which is positioned substantially in alignment with the center, c, or axel of the at least one wheel 34. The at least one wheel 34 is further mounted to the base portion 32, such that the radius of the wheel, r, is smaller than a distance D from c to the floor contacting surface 36*a* of the base portion 32. This creates a smaller distance d between the bottom of the at least one wheel 34 and the floor 28, which spaces or raises the at least one wheel 34 from the floor 28 in the stationary orientation.

In a further preferred embodiment, as seen in FIGS. 1A-1B, a center of mass 38 of the air management system 10 is positioned relatively forward relative to the axis toward a front 40 of the air management system 10 in the stationary orientation. In an example, the center of mass 38 of the caddy 10*a* is located forward of the axel of the at least one wheel 34 in the stationary orientation, between a front face 40 of the caddy 10*a* and the axel of the at least one wheel 34.

In the mobile orientation, the center of mass 38 of the air management system 10 is positioned relatively over the axis in the mobile orientation. In an example, the center of mass 38 of the caddy 10*a* is located relatively above and closer to the center c of the at least one wheel 34, creating an ergonomic advantage for moving or transporting the caddy 10*a*. The handle 44 is configured to be mounted to the base portion 32 and the handle 44 can be manipulated to shift the caddy 10*a* into the mobile orientation and shift the center of mass 38 relatively above or over center c of the at least one wheel 34, thereby allowing the caddy 10*a* to be easily guided for movement relative to the floor 28.

Figure 1C:
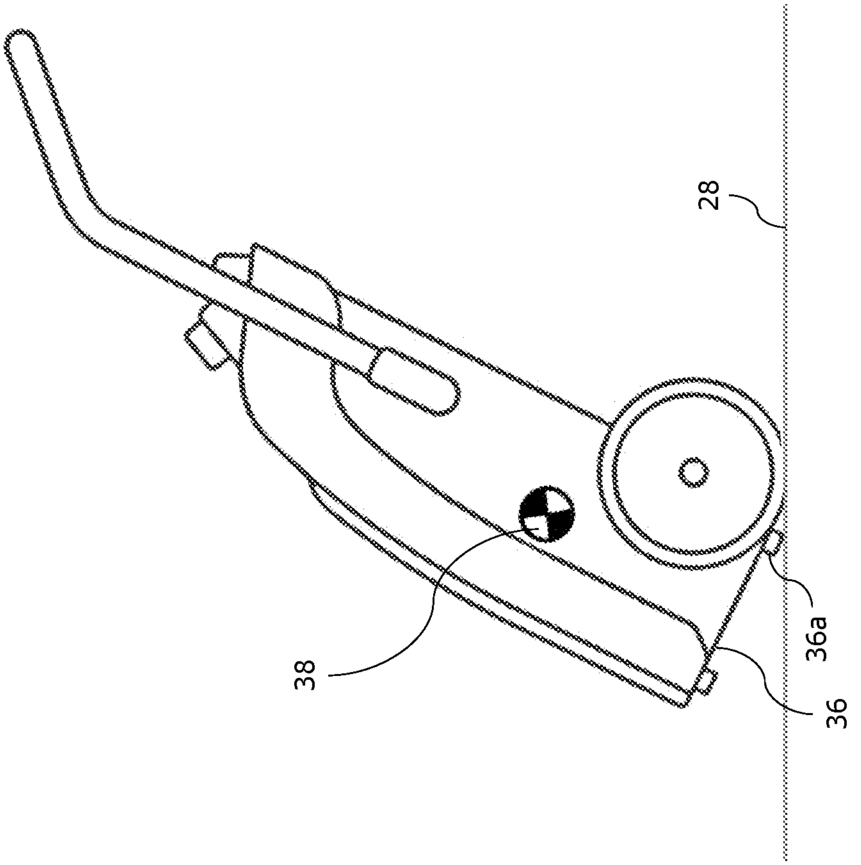
FIG. 1C is a side view of the embodiment of FIG. 1A, showing an angle in which the embodiment in a mobile orientation has a tendency to revert to the stationary orientation.

In a further preferred embodiment, as illustrated in FIG. 1C, when the center of mass 38 of the air management system 10 is positioned between the axis and the front 42 of the air management system 10, the air management system 10 will tend to move from the mobile orientation to the stationary orientation when released from the mobile orientation. In an example, the center of mass 38 of the base portion 32 of the caddy 10*a* is positioned such that if the handle 44 of the caddy 10*a* is released within the range of angles between the stationary position and the mobile orientation, the caddy 10*a* will tend to revert to the stationary orientation.

Figure 7:
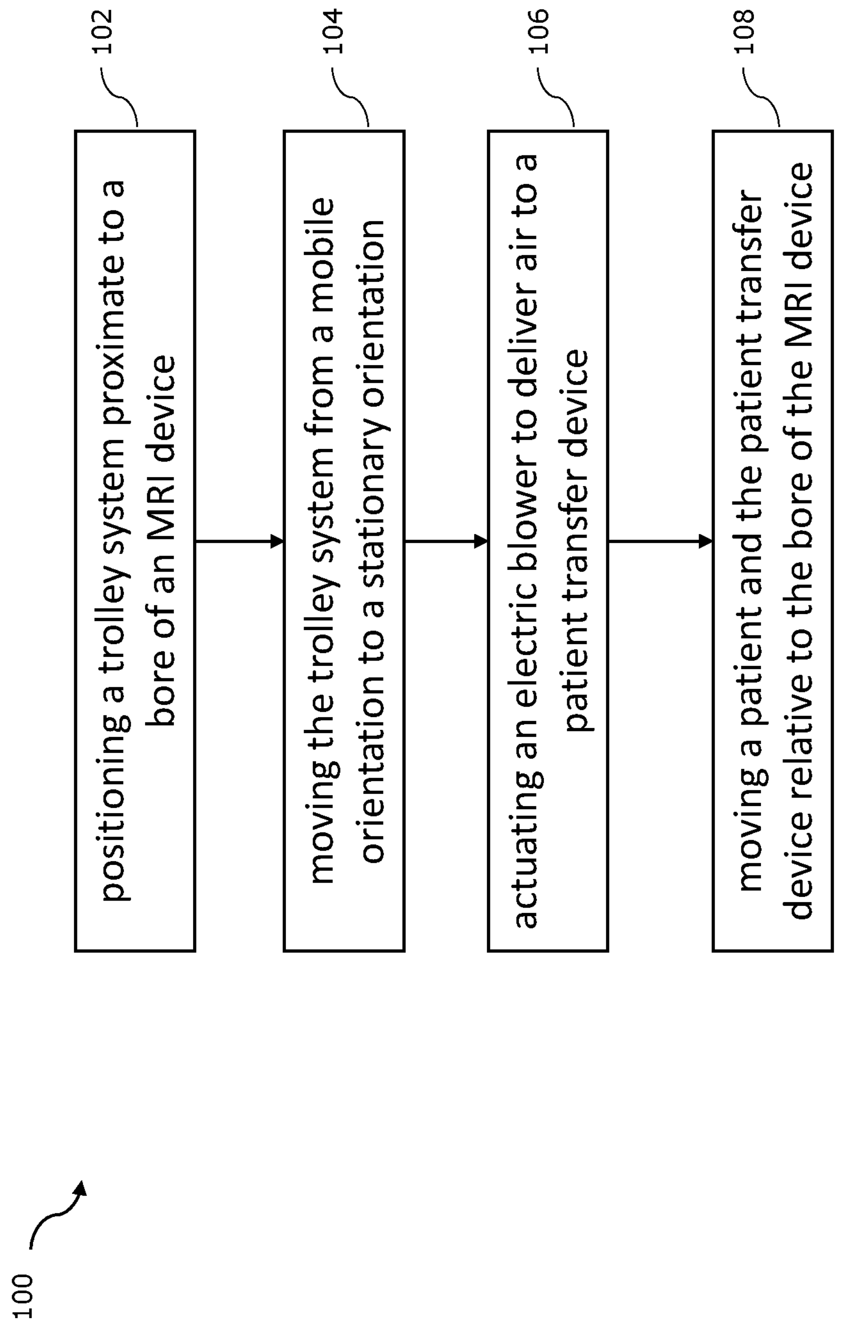
FIG. 7 is a diagram illustrating an embodiment of a method of operating the embodiment of the air management system of FIG. 1A.

Referring now to FIG. 7, a method 100 of moving a patient relative to a bore of an MRI device using a patient transfer device is provided. The method 100 includes steps of positioning a caddy proximate to the bore of the MRI device, moving the caddy from a mobile orientation to a stationary orientation, actuating an electric blower to move air, such as deliver or withdraw air, to the patient transfer device, moving a patient and the patient transfer device relative to the bore of the MRI device. Additional details of method 100 are set forth below with respect to the features of air management system 10.

In step 102, a caddy is positioned proximate to the bore of an MRI device. In an example, a air management system 10 is positioned proximate to the bore of the MRI device 12 and the air management system 10 is MR Compatible with a maximum magnetic attraction force less than or equal to 50 lbs force. The air management system 10 further comprises a base portion 32 configured for movement relative to a floor 28. The air management system 10 also includes at least one wheel 34 coupled to the base portion 32 and positioned for movement of the base portion 32 relative to the floor 28. In addition, an electric blower 24 is mounted to the base portion 32, such as in a central or lower region of the base portion 32. The blower 24 is positioned in such a way that the electric blower 24 remains within a relatively weaker portion of a magnetic field generated by the bore of the MRI device 12 (such as the magnetic field profile illustrated in FIG. 2), thereby reducing the effect of the magnetic field on the operation of the electric blower 24 during use of the electric blower 24. Further, an optional step 102 includes positioning the at least one wheel 34 to contact the floor 28 to permit the movement of the air management system 10 relative to the floor 28 in a mobile orientation.

In step 104, a caddy is moved from a mobile orientation to a stationary orientation. In an example, the air management system 10 having the base portion 32 is moved from the mobile orientation, in which the at least one wheel 34 facilitates the movement of the air management system 10 relative to the floor 28, to the stationary orientation, in which the at least one wheel 34 is prevented from facilitating the movement of the air management system 10 relative to the floor 28. Further, an optional step 104 includes spacing or raising the at least one wheel 34 from the floor 28 for the distance, d, to prevent the at least one wheel 34 from facilitating the movement of the air management system 10 relative to the floor 28 in the stationary orientation.

In step 106, an electric blower is actuated to deliver air to a patient transfer device. In an example, the electric blower 24 is actuated to move air, such as deliver or withdraw air, to the patient transfer device 18 to facilitate movement of a patient 58. The electric blower 24 remains in operation while adjacent to the bore of the MRI device 12 and while the magnetic field is being generated by the bore of the MRI device 12 (such as the magnetic field profile illustrated in FIG. 2).

In step 108, the patient transfer device 18 is moved relative to the bore of the MRI device 12.

Method 100 may further include the air management system 10 being configured for use with a patient support portion 20 configured to support the patient 58. Method 100 may further comprise moving the patient 58 and the patient transfer device 18 relative to the patient support portion 20.

Example

Figure 8B:
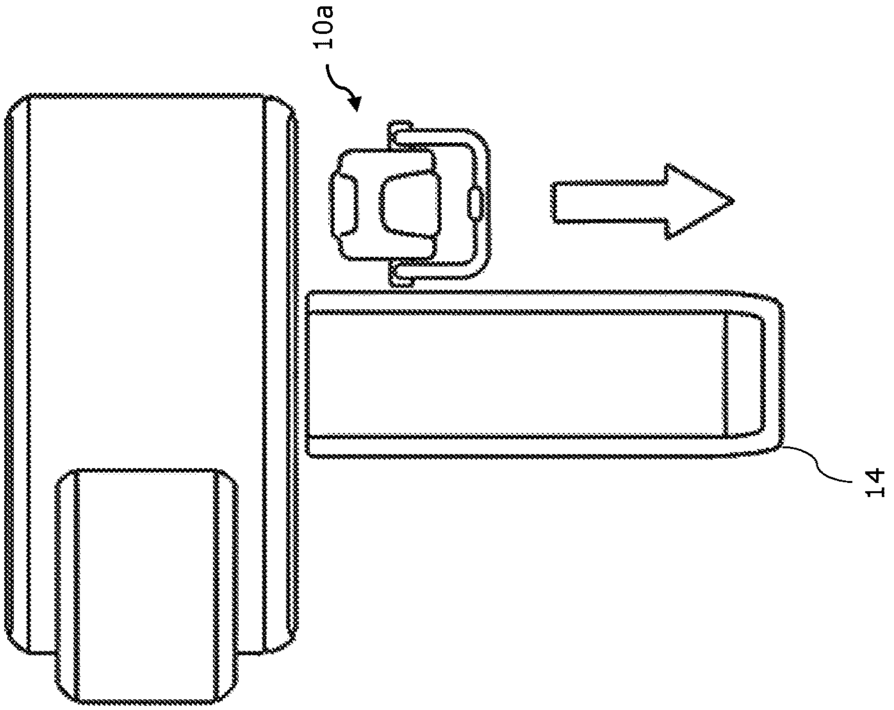
FIGS. 8A-8B depict top plan views of the relative position of the embodiment of FIG. 1A and an MRI device when determining the pull force on the air management system in lateral and longitudinal directions, respectively.
Figure 8A:
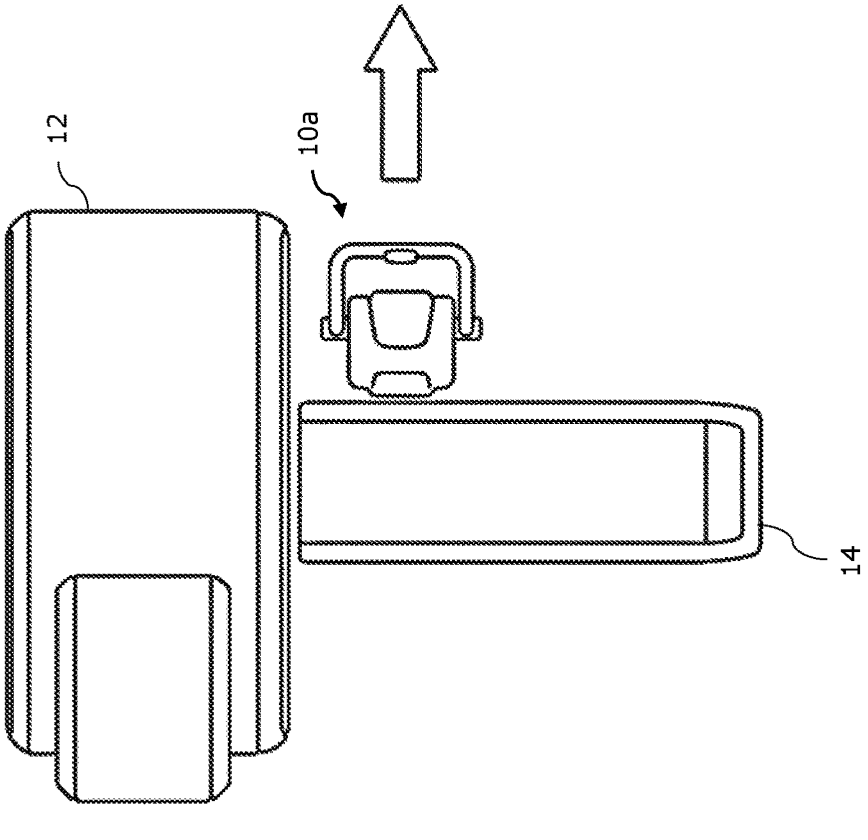

The caddy was introduced into the MRI environment. The MRI scanner used in the below test was a Siemens MAGNETOM Prisma 3T MRI scanner. The caddy was placed adjacent to the scanner table, facing the bore. The caddy was moved towards the bore until a magnetic field detector indicated that the caddy had crossed the 30 Gauss field strength boundary. The caddy was returned to the stationary orientation and moved backwards until the alarm stopped. The distance from the front of the caddy to the face of the bore was measured, and the axel position was marked with tape. A force measurement to move along the floor was taken by balancing the caddy on its wheels and pulling on a strap attached to the hose inlet until the caddy begins to roll (the longitudinal position). The longitudinal position is illustrated in FIG. 8B. The caddy was then rotated 90 degrees, such that it faces the MRI table. The caddy was centered on the tape used to initially mark the axel. The force to move measurement was taken again in this position (the lateral position). The lateral position is illustrated in FIG. 8A. This procedure was repeated for the 100 Gauss field strength boundary, the force of noticeable attraction location, half distance from noticeable attraction location, and against the bore of the MRI apparatus. The function of the electrical blower incorporated in the caddy was also assessed at each of these locations. The results are summarized in the table below.

| Device Location (Distance from face of MRI Bore) | Test Orientation (relative to MR table) | Force (lbs force) | Force (N) | Blower Functional? |
|---|---|---|---|---|
| Baseline (outside MRI room) | N/a | 2 | 8.9 | Yes |
| 30 Gauss Alarm Point | Longitudinal | 1.5 | 6.7 | Yes |
| (86 in) | Lateral | 2 | 8.9 | Yes |
| 100 Gauss Alarm | Longitudinal | 2 | 8.9 | Yes |
| Point (53 in) | Lateral | 2 | 8.9 | Yes |
| Point of Noticeable | Longitudinal | 2 | 8.9 | Yes |
| Attraction (24 in) | Lateral | 2 | 8.9 | Yes |
| Half distance from Noticeable Attraction | Longitudinal | 5 | 22.2 | Yes |
| (12 in) | Lateral | 3.5 | 15.6 | Yes |
| Against Face of MRI | Longitudinal | 22.5 | 100.1 | Yes |
| Bore | Lateral | 8.5 | 37.8 | Yes |

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An air caddy operable within an MRI room and adjacent an MRI apparatus in the MRI room, the caddy being configured for permitting continuous contact with a floor of the MRI room and movement along the floor of the MRI room, the caddy comprising:

a base portion having at least one wheel positioned to selectively permit movement of the caddy relative to a floor, the base portion being movable between a mobile orientation in which the at least one wheel facilitates the movement of the caddy relative to the floor and a stationary orientation in which the at least one wheel is prevented from facilitating the movement of the caddy relative to the floor;

an electric blower coupled to the base portion of the caddy and fixed to prevent movement of the electric blower relative to the caddy, the electric blower being configured to move air when the base portion is in the stationary orientation, and the relative position of the blower to the MRI apparatus in the MRI room does not change when the blower moves air and when the base portion is in the stationary orientation, the electric blower being mounted such that the electric blower remains within a weaker portion of a magnetic field generated by the MRI apparatus in the MRI room; and a battery for powering the electric blower, wherein at least one of the battery and the electric blower is located within a central region of the base portion, thereby reducing the effect of the magnetic field on the operation of the electric blower during use of the electric blower;

wherein the caddy is MR Compatible with a maximum magnetic attraction force less than or equal to 50 lbs force; and wherein the caddy is positionable adjacent the MRI apparatus within the MRI room and the magnetic field of the MRI apparatus does not interfere with the operation of the electric blower when the caddy is positioned adjacent the MRI apparatus, such that the electric blower operates while adjacent the MRI apparatus and while the magnetic field is generated by the MRI apparatus;

a supplemental mass mounted to the caddy and configured to both prevent the caddy from leaving the continuous contact with the floor of the MRI room in response to a magnetic force of attraction generated by the MRI apparatus and to maintain the center of gravity such that the caddy is biased to move toward the stationary orientation from the mobile orientation, the supplemental mass also being integrally formed with the base portion, the electric blower, or a frame of the caddy as a single body of unitary construction.

2. The caddy of claim 1, the caddy being a caddy for movement of the electric blower relative to a patient transfer device that is configured for movement relative to a patient support, the electric blower being configured to move air to the patient transfer device.

3. The caddy of claim 2, the patient transfer device providing an air bearing, and the electric blower being configured to move air to the air bearing.

4. The caddy of claim 1, further comprising at least two wheels positioned for movement of the caddy relative to the floor.

5. The caddy of claim 1, wherein the caddy is MR Compatible with a maximum magnetic attraction force less than or equal to 25 lbs force.

6. The caddy of claim 1, the at least one wheel being positioned to contact the floor to permit movement of the caddy relative to the floor when the base portion is in the mobile orientation, and the at least one wheel being spaced from the floor to be prevented from facilitating the movement of the caddy relative to the floor when the base portion is positioned in the stationary orientation.

7. The caddy of claim 1, wherein the at least one wheel can be locked to retain the caddy in the stationary orientation and unlocked to revert to the mobile orientation.

8. The caddy of claim 1, the base portion having a bottom surface comprising at least one floor-contacting surface positioned to elevate the at least one wheel from the floor when the base portion is in the stationary orientation.

9. The caddy of claim 1, the at least one wheel being mounted to rotate about an axis that is fixed in position relative to the base portion of the caddy.

10. The caddy of claim 1, wherein air is movable by the electric blower to or from at least one of a patient transfer device, a patient bed, a wound care bed, a bed that provides alternating pressures, a surface designed for therapeutic applications, a surface designed for patient comfort, a skin protection surface, an air powered device, a vacuum cushion and a compression surface.

11. The caddy of claim 1, wherein the electric blower of the caddy is configured to be coupled to a patient transfer device for moving air to an air bearing of the patient transfer device.

12. The caddy of claim 1, comprising two or more wheels.

13. The caddy of claim 1, further comprising a handle mounted to the base portion to facilitate movement of the caddy.

14. An air caddy operable within an MRI room and adjacent an MRI apparatus in the MRI room, the caddy being configured for permitting continuous contact with a floor of the MRI room and movement along the floor of the MRI room, the caddy comprising:

a base portion having at least one wheel positioned to selectively permit movement of the caddy relative to a floor, the base portion being movable between a mobile orientation in which the at least one wheel facilitates the movement of the caddy relative to the floor and a stationary orientation in which the at least one wheel is prevented from facilitating the movement of the caddy relative to the floor, the at least one wheel being mounted to rotate about an axis that is fixed in position relative to the base portion of the caddy; and an electric blower coupled to the base portion of the caddy and fixed to prevent movement of the electric blower relative to the caddy, the electric blower being configured to move air when the base portion is in the stationary orientation, and the relative position of the blower to the MRI apparatus in the MRI room does not change when the blower moves air and when the base portion is in the stationary orientation, the electric blower being mounted such that the electric blower remains within a weaker portion of a magnetic field generated by the MRI apparatus in the MRI room, thereby reducing the effect of the magnetic field on the operation of the electric blower during use of the electric blower;

wherein the caddy is MR Compatible with a maximum magnetic attraction force less than or equal to 50 lbs force; and wherein the caddy is positionable adjacent the MRI apparatus within the MRI room and the magnetic field of the MRI apparatus does not interfere with the operation of the electric blower when the caddy is positioned adjacent the MRI apparatus, such that the electric blower operates while adjacent the MRI apparatus and while the magnetic field is generated by the MRI apparatus;

wherein a distance from the axis to at least one floor-contacting surface of the base portion is greater than a distance from the axis to a floor-contacting surface of the at least one wheel.

15. An air caddy operable within an MRI room and adjacent an MRI apparatus in the MRI room, the caddy being configured for permitting continuous contact with a floor of the MRI room and movement along the floor of the MRI room, the caddy comprising:

a base portion having at least one wheel positioned to selectively permit movement of the caddy relative to a floor, the base portion being movable between a mobile orientation in which the at least one wheel facilitates the movement of the caddy relative to the floor and a stationary orientation in which the at least one wheel is prevented from facilitating the movement of the caddy relative to the floor, the at least one wheel being mounted to rotate about an axis that is fixed in position relative to the base portion of the caddy; and an electric blower coupled to the base portion of the caddy and fixed to prevent movement of the electric blower relative to the caddy, the electric blower being configured to move air when the base portion is in the stationary orientation, and the relative position of the blower to the MRI apparatus in the MRI room does not change when the blower moves air and when the base portion is in the stationary orientation, the electric blower being mounted such that the electric blower remains within a weaker portion of a magnetic field generated by the MRI apparatus in the MRI room, thereby reducing the effect of the magnetic field on the operation of the electric blower during use of the electric blower;

wherein the caddy is MR Compatible with a maximum magnetic attraction force less than or equal to 50 lbs force; and wherein the caddy is positionable adjacent the MRI apparatus within the MRI room and the magnetic field of the MRI apparatus does not interfere with the operation of the electric blower when the caddy is positioned adjacent the MRI apparatus, such that the electric blower operates while adjacent the MRI apparatus and while the magnetic field is generated by the MRI apparatus, wherein the center of mass of the caddy is positioned relatively forward relative to the axis toward a front of the caddy in the stationary orientation, and wherein the center of mass is positioned relatively over the axis in the mobile orientation.

16. The caddy of claim 15, wherein the center of mass of the caddy is positioned between the axis and the front of the caddy such that the caddy moves from the mobile orientation to the stationary orientation when released from the mobile orientation.

17. The caddy of claim 15, further comprising a supplemental mass mounted to the caddy to provide a threshold mass.

18. The caddy of claim 17, the supplemental mass providing the threshold mass selected such that the caddy is prevented from leaving the continuous contact with the floor of the MRI room in response to a magnetic force of attraction generated by the MRI apparatus.

19. The caddy of claim 18, the supplemental mass being selected to overcome the magnetic force of attraction when the caddy is in the continuous contact with the floor of the MRI room and directly adjacent to the MRI apparatus when the MRI apparatus is operated to generate a magnetic field.

20. The caddy of claim 17, the supplemental mass providing the threshold mass such that the caddy maintains a desired center of gravity.

21. The caddy of claim 20, the supplemental mass being positioned to maintain the center of gravity such that the caddy is biased to move toward the stationary orientation from the mobile orientation.

22. The caddy of claim 17, the supplemental mass being configured to both prevent the caddy from leaving the continuous contact with the floor of the MRI room in response to a magnetic force of attraction generated by the MRI apparatus and to maintain the center of gravity such that the caddy is biased to move toward the stationary orientation from the mobile orientation.

23. The caddy of claim 17, the supplemental mass being non-magnetic.

24. A method of moving a patient relative to a bore of an MRI device using a patient transfer device, the method comprising:

positioning a caddy proximate to the bore of the MRI device, the caddy being MR Compatible with a maximum magnetic attraction force less than or equal to 50 lbs force and including:

a base portion configured for movement relative to a floor, at least one wheel coupled to the base portion and positioned for movement of the base portion relative to the floor, and an electric blower, the electric blower being mounted such that the electric blower remains within a weaker portion of a magnetic field generated by the bore of the MRI device, thereby reducing the effect of the magnetic field on the operation of the electric blower during use of the electric blower, a battery for powering the electric blower, wherein at least one of the battery and the electric blower is located within a central region of the base portion, thereby reducing the effect of the magnetic field on the operation of the electric blower during use of the electric blower, and a supplemental mass mounted to the caddy and configured to both prevent the caddy from leaving the continuous contact with the floor of the MRI room in response to a magnetic force of attraction generated by the MRI apparatus and to maintain the center of gravity such that the caddy is biased to move toward the stationary orientation from the mobile orientation, the supplemental mass also being integrally formed with the base portion, the electric blower, or a frame of the caddy as a single body of unitary construction;

moving the base portion from a mobile orientation in which the at least one wheel facilitates the movement of the caddy relative to the floor to a stationary orientation in which the at least one wheel is prevented from facilitating the movement of the caddy relative to the floor; and actuating the electric blower to move air to the patient transfer device, thereby moving air to or from the patient transfer device to facilitate movement of the patient, the electric blower operating while adjacent the bore of the MRI device and while the magnetic field is being generated by the bore of the MRI device; and moving the patient and the patient transfer device relative to the bore of the MRI device.

25. The method of claim 24, the caddy being configured for use with a patient support portion configured to support the patient, the method further comprising moving the patient and the patient transfer device relative to the patient support portion.

26. A method of moving a patient relative to a bore of an MRI device using a patient transfer device, the method comprising:

positioning a caddy proximate to the bore of the MRI device, the caddy being MR Compatible with a maximum magnetic attraction force less than or equal to 50 lbs force and including:

a base portion configured for movement relative to a floor, at least one wheel coupled to the base portion and positioned for movement of the base portion relative to the floor, the at least one wheel being mounted to rotate about an axis that is fixed in position relative to the base portion, and an electric blower, the electric blower being mounted such that the electric blower remains within a weaker portion of a magnetic field generated by the bore of the MRI device, thereby reducing the effect of the magnetic field on the operation of the electric blower during use of the electric blower, wherein a distance from the axis to the at least one floor-contacting surface of the base portion is greater than a distance from the axis to a floor-contacting surface of the at least one wheel; and moving the base portion from a mobile orientation in which the at least one wheel facilitates the movement of the caddy relative to the floor to a stationary orientation in which the at least one wheel is prevented from facilitating the movement of the caddy relative to the floor;

actuating the electric blower to move air to the patient transfer device, thereby moving air to or from the patient transfer device to facilitate movement of the patient, the electric blower operating while adjacent the bore of the MRI device and while the magnetic field is being generated by the bore of the MRI device; and moving the patient and the patient transfer device relative to the bore of the MRI device.

27. A method of moving a patient relative to a bore of an MRI device using a patient transfer device, the method comprising:

positioning a caddy proximate to the bore of the MRI device, the caddy being MR Compatible with a maximum magnetic attraction force less than or equal to 50 lbs force and including:

a base portion configured for movement relative to a floor, at least one wheel coupled to the base portion and positioned for movement of the base portion relative to the floor, and an electric blower, the electric blower being mounted such that the electric blower remains within a weaker portion of a magnetic field generated by the bore of the MRI device, thereby reducing the effect of the magnetic field on the operation of the electric blower during use of the electric blower, the at least one wheel being mounted to rotate about an axis that is fixed in position relative to the base portion of the caddy, and wherein the center of mass of the caddy is positioned relatively forward relative to the axis toward a front of the caddy in the stationary orientation, and wherein the center of mass is positioned relatively over the axis in the mobile orientation; and moving the base portion from a mobile orientation in which the at least one wheel facilitates the movement of the caddy relative to the floor to a stationary orientation in which the at least one wheel is prevented from facilitating the movement of the caddy relative to the floor;

actuating the electric blower to move air to the patient transfer device, thereby moving air to or from the patient transfer device to facilitate movement of the patient, the electric blower operating while adjacent the bore of the MRI device and while the magnetic field is being generated by the bore of the MRI device; and moving the patient and the patient transfer device relative to the bore of the MRI device.

* * * * *